United States Patent [19]
Chan

[11] Patent Number: 5,137,578
[45] Date of Patent: Aug. 11, 1992

[54] SMOKING COMPOSITIONS CONTAINING A FLAVORANT-RELEASE SACCHARIDE ADDITIVE

[75] Inventor: Wootung G. Chan, Chesterfield, Va.

[73] Assignees: Philip Morris Incorporated, New York, N.Y.; Philip Morris Products Inc., Richmond, Va.

[21] Appl. No.: 660,881

[22] Filed: Feb. 26, 1991

[51] Int. Cl.$^5$ ............... A24B 15/36; C07D 319/02
[52] U.S. Cl. ................................ 131/277; 549/365; 523/100
[58] Field of Search ............. 131/277; 549/365; 523/100

[56] References Cited

FOREIGN PATENT DOCUMENTS 2012826  3/1990  Canada .

Primary Examiner—V. Millin
Attorney, Agent, or Firm—James E. Schardt

[57] ABSTRACT

This invention provides smoking compositions which contain a novel flavorant-release additive.

Under cigarette smoking conditions, a combustible filler and/or paper wrapper additive such as 4'-formyl-2'-methoxyphenyl 4,6-O-cinnamylidene-$\beta$-D-glucopyranoside pyrolyzes into cinnamaldehyde and vanillin flavorants as volatile components of the cigarette smoke.

20 Claims, No Drawings

SMOKING COMPOSITIONS CONTAINING A FLAVORANT-RELEASE SACCHARIDE ADDITIVE

BACKGROUND OF THE INVENTION

A variety of flavorants have been developed and proposed for incorporation into tobacco products. Illustrative of such tobacco flavorants are those described in U.S. Pat. Nos. 3,580,259; 3,625,224; 3,722,516; 3,750,674; 3,879,425; 3,881,025; 3,884,247; 3,890,981; 3,903,900; 3,914,451; 3,915,175; 3,920,027; 3,924,644; 3,937,228; 3,943,943; 3,568,387; 3,379,754; and the like.

J. C. Leffingwell et al "Tobacco Flavoring For Smoking Products (R. J. Reynolds publication, 1972) recites a listing of desirable flavorants for smoking compositions, which include phenols, terpenols and lactones such as guaiacol, 1-undecanol and 5-dodecalactone.

The high degree of volatility and ease of sublimation of flavorant additives in tobacco products have presented problems in the manufacturing operations, and have resulted in a decreased shelf-life of the products due to losses of flavorant by evaporation on storage.

Recent developments have involved incorporating a low volatility organic additive to a smoking composition, which under smoking conditions is pyrolyzed into one or more fragments that function to improve the taste and character of mainstream tobacco smoke, and in some cases a consequential improvement of sidestream smoke aroma.

U.S. Pat. No. 3,312,226 describes smoking tobacco compositions which contain an ester additive such as 1-menthyl linalool carbonate. Under smoking conditions pyrolysis of the carbonate ester releases menthol which flavors the mainstream smoke.

U.S. Pat. No. 3,332,428 and U.S. Pat. No. 3,419,543 describe smoking tobacco compositions which contain a menthyl carbonate ester of a glycol or saccharide, which under smoking conditions decomposes to release free menthol into the mainstream smoke. U.S. Pat. No. 3,499,452 discloses similar smoking tobacco compositions in which a carbonate ester additive releases flavorant volatiles other than menthol.

U.S. Pat. Nos. 4,119,106; 4,171,702; 4,177,339; and 4,212,310 describe other oligomeric and polymeric carbonate ester derivatives which as constituents of smoking compositions are stable and non-volatile under storage conditions, and are adapted to release pyrolysis products under smoking conditions that improve the taste and aroma of smoke.

U.S. Pat. Nos. 4,036,237; 4,141,906; and 4,178,458 describe β-hydroxyesters which as additives in smoking compositions pyrolyze into volatile aldehyde and ester flavorants under smoking conditions.

Of specific interest with respect to the present invention is the proposed utilization of an organic additive to a cigarette paper wrapper to enhance sidestream smoke aroma under smoking conditions. U.S. Pat. No. 4,804,002 describes a tobacco product wrapper containing a flavorant additive comprising a glycoside of a carbohydrate and phenolic compound. Under cigarette smoking conditions a flavorant additive such as ethyl vanillyl-D-glucoside yields ethyl vanillin and levoglucosan as pyrolysis products.

There is continuing research effort to develop low delivery smoking compositions which generate mainstream smoke with enhanced taste and sidestream smoke with a pleasant aroma under smoking conditions.

Accordingly, it is an object of this invention to provide smoking compositions having incorporated therein a flavorant-release component which is characterized by lack of mobility and/or volatility at ambient temperature.

It is another object of this invention to provide cigarette smoking products having a paper wrapper which has incorporated therein a flavorant-release additive which under normal smoking conditions imparts improved aroma to sidestream smoke.

It is a further object of this invention to provide novel glucopyranose and qlucopyranoside acetals and ketals which are adapted to be incorporated into cigarette filler and/or paper wrapper components, and which under normal smoking conditions release a volatile carbonyl flavorant into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001–5 weight percent, based on the total weight of filler, of a flavorant-release additive corresponding to the formula:

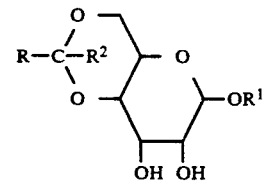

where R—C= is a $C_7$-$C_{12}$ benzylidene or $C_9$-$C_{15}$ cinnamylidene structure, $R^1$ is hydrogen or a $C_6$-$C_{10}$ aromatic substituent, and $R^2$ is hydrogen or a $C_1$-$C_6$ alkyl substituent.

In another embodiment this invention provides a cigarette smoking product comprising (1) a combustible filler selected from natural tobacco, reconstituted tobacco and tobacco substitutes, and (2) a paper wrapper which has incorporated therein a flavorant-release additive corresponding to the formula:

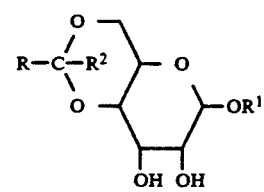

where R—C= is a $C_7$-$C_{12}$ benzylidene or $C_9$-$C_{15}$ cinnamylidene structure, $R^1$ is hydrogen or a $C_6$-$C_{10}$ aromatic substituent, and $R^2$ is hydrogen or a $C_1$-$C_6$ alkyl substituent.

Illustrative of the R—C= divalent radical in the above represented flavorant-release additive formula are structures which are derived from benzaldehyde having one or more substituents which include hydroxy, $C_1$-$C_6$ alkyl, $C_1$-$C_6$ alkoxy, $C_1$-$C_6$ alkanoyl, and the like; or derived from cinnamaldehyde having similar ring substituents as the benzaldehyde structure, or having substituents such as $C_1-C_6$ alkyl on the ethylenic sidechain.

Illustrative of the $R^1$ substituent in the additive formula are structures which are derived from phenols such as vanillin, ethyl vanillin, thymol, guaiacol, methyl salicylate, eugenol, and the like.

The $R^1$ substituent in the additive formula also can be a saccharide structure, which taken together with the pyranose elements can represent a disaccharide such as cellobiose or lactose.

Illustrative of the $R^2$ substituent are hydrogen, methyl, ethyl, propyl, isopropyl, butyl, isobutyl, 2-butyl, pentyl, hexyl, and the like.

The pyranose or pyranoside structure in the additive formula is derived from an aldohexose such as glucose, mannose, galactose, and the like.

A cigarette smoking product with treated paper wrapper in accordance with the present invention typically contains between about 0.01-5 weight percent of flavorant-release additive in the paper wrapper.

In a further embodiment an invention cigarette product contains between about 0.01-5 weight percent of flavorant-release additive in the paper wrapper, and contains between about 0.0001-5 weight percent of flavorant-release additive in the combustible filler, based on the weight of filler.

A present invention flavorant-release additive which is incorporated in smoking compositions as described above is a low volatility compound which under normal smoking conditions in the case of a preferred species pyrolyzes into two volatile constituents, both of which enhance the flavor and aroma of low delivery cigarette smoke:

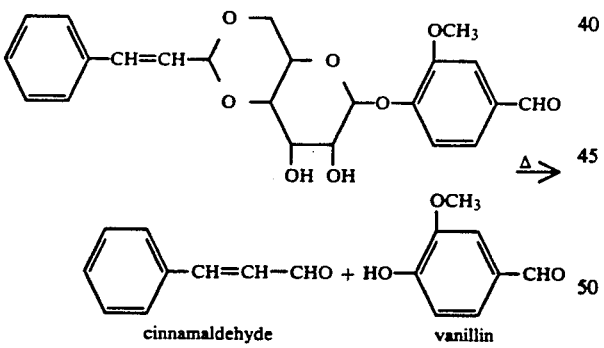

An important feature of the above illustrated invention smoking composition is the release of two aromatic flavorants under smoking conditions, one of which is a cinnamaldehyde type structure.

Both the cinnamaldehyde and vanillin volatiles which are released have exceptional organoleptic properties. Each of the compounds contributes a pleasant flavor and aroma to cigarette smoke.

Preparation Of Flavorant-release Compounds

One method of preparing the invention flavorant-release compounds is by the condensation of a benzaldehyde or cinnamaldehyde type reactant with a hexoaldose derivative:

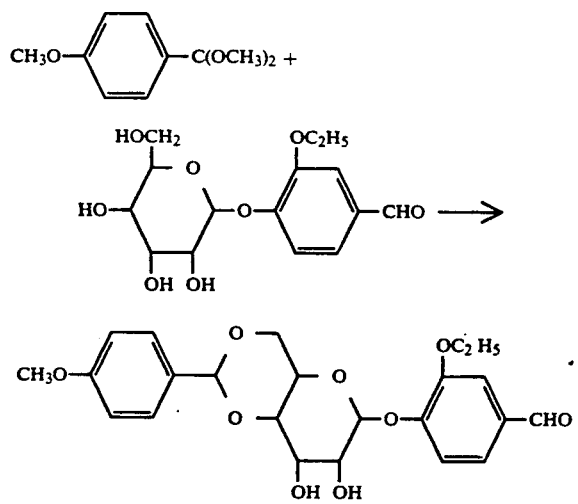

The ethyl vanillin reactant in the above illustrated flow diagram is obtained by a synthesis procedure similar to that described in U.S. Pat. No. 4,804,002.

Reaction conditions for mild acid-catalyzed transacetalation of aldehyde acetals with saccharides are described in technical publications which include Carbohyd. Res., 21, 473(1972); Tetrahedron Lett., 29 (No. 9), 991(1988); and Aust. J. Chem., 41, 91(1988).

Preparation Of Tobacco Compositions

In a further embodiment the present invention provides a method of preparing a smoking composition which is adapted to impart flavor and aroma to mainstream and sidestream smoke under conditions, which method comprises incorporating into natural tobacco, reconstituted tobacco or tobacco substitute between about 0.0001-5 weight percent, based on composition weight, of a flavorant-release additive corresponding to the formula:

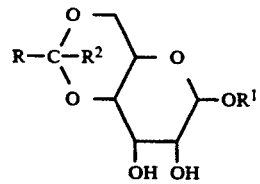

where $R-C=$ is a $C_7-C_{12}$ benzylidene or $C_9-C_{15}$ cinnamylidene structure, $R^1$ is hydrogen or a $C_6-C_{10}$ aromatic substituent, and $R^2$ is hydrogen or a $C_1-C_6$ alkyl substituent.

The invention flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

As previously described hereinabove, an invention flavorant-release additive also can be incorporated in the paper wrapper of cigarette products, for the purpose of enhancing the aroma of cigarette sidestream smoke under smoking conditions.

The following Examples are further illustrative of the present invention. The specific ingredients and processing parameters are presented as being typical, and various modifications can be derived in view of the foregoing disclosure within the scope of the invention.

EXAMPLE I

4'-Formyl-2,'-methoxyphenyl 4,6-O-(α-hexylcinnamylidene)-β-D-glucopyranoside

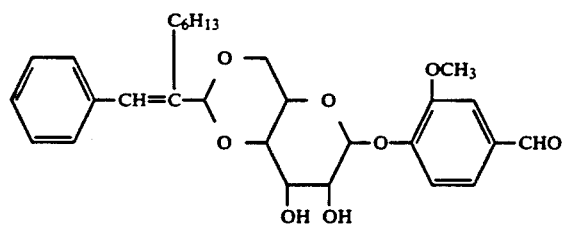

A 3.14 g (10 mmole) quantity of glucovanillin and 0.5 g of Amberlite® IR-120 (Rohm & Haas Co.) were mixed with 40 ml of acetonitrile, and the admixture was heated to reflux. A total of three 2.6 g (10 mmole) quantities of a α-hexylcinnamylaldehyde dimethyl acetal were added in one hour intervals. After the additions were completed, the heating at reflux was continued for an additional hour. The reaction medium then was cooled to room temperature, and the ion exchange resin catalyst was removed by filtration. After removal of solvent by rotary evaporation under vacuum, the residual syrup was distilled by Kugelrohr at a pot temperature of <115° C. and a vacuum of <0.3 mm Hg. The residue after distillation was recrystallized from 95% ethanol to yield 4 g of product. NMR and IR spectra confirmed the title compound structure.

EXAMPLE II

4'-Formyl-2'-methoxyphenyl 4,6-O-(α-amylcinnamylidene)-β-D-glucopyranoside

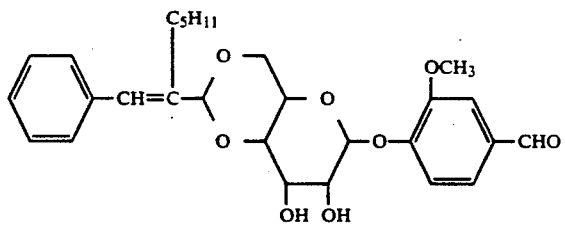

The title compound was prepared following the procedures of Example I, using 3.14 g (10 mmole) of glucovanillin and 3×2.5 g (30 mmole) of α-amylcinnamylaldehyde dimethyl acetal. After recrystallization from 95% ethanol, 4.5 g of product was obtained. NMR and IR spectra confirmed the title compound structure.

EXAMPLE III

4'-Formyl-2'-methoxyphenyl 4,6-O-cinnamylidene-β-D-glucopyranoside

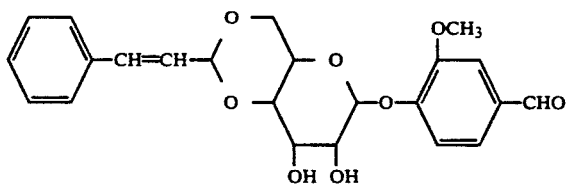

The title compound was prepared following the procedures of Example I, using 3.14 g of glucovanillin (10 mmole) and 3×1.8 g of cinnamylaldehyde dimethyl acetal (30 mmole). After recrystallization from 95% ethanol, 3 g of product was obtained. NMR and IR spectra confirmed the title compound structure.

EXAMPLE IV

2'-Methoxy-4'-methylphenyl 4,6-O-(α-hexylcinnamylidene)-α-D-glucopyranoside

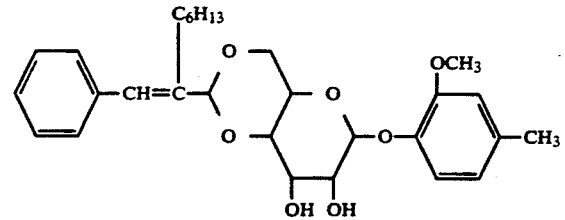

The title compound was prepared following the procedures of Example I, using 3 g (10 mmole) of 2'-methoxy-4'-methylphenyl α-D-glucopyranoside and 3×2.6 g (30 mmole) of α-hexylcinnamylaldehyde dimethyl acetal. After recrystallization from acetone, 3.8 g of product was obtained. NMR and IR spectra confirmed the title compound structure.

EXAMPLE V

4-6-O-Cinnamylidene-D-glucopyranose

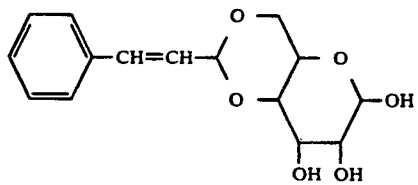

A 1.8 g quantity of glucose was dissolved in 40 ml of dimethylformamide, and 1 g amount of Amberlite ® IR-120 was added. The mixture was heated to 80° C., and a total of three 1.78 g quantities of cinnamylaldehyde dimethyl acetal were added in one hour intervals. After the additions were completed, the mixture was heated for an additional hour. The ion exchange resin catalyst was removed by filtration, and the solvent and excess cinnamylaldehyde dimethyl acetal were removed by vacuum distillation. The residual material was recrystallized from 95% ethanol to give 1.5 g of product. NMR and IR spectra confirmed the title compound structure.

EXAMPLE VI

4,6-O-(α-Amylcinnamylidene)-D-glucopyranose

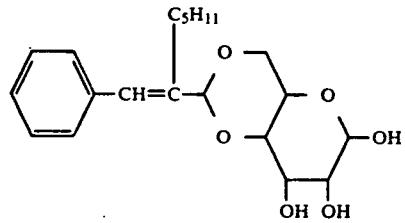

The title compound was prepared following the procedures of Example V, using 3.6 g (20 mmole) of glucose and 3×4.96 g (60 mmole) of α-amylcinnamylaldehyde dimethyl acetal in 80 ml of dimethylformamide. After recrystallization from 95% ethanol (containing a few drops of concentrated ammonium hydroxide), 5.5 g of product was obtained. NMR and IR spectra confirmed the title compound structure.

EXAMPLE VII

4,6-O-(α-Hexylcinnamylidene)-D-glucopyranose

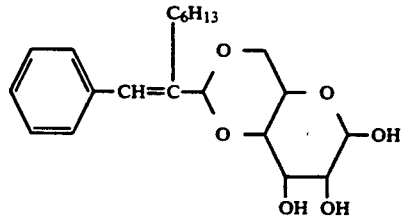

The title compound was prepared following the procedures of Example V, using 3.6 g of glucose (20 mmole) and 3×5.14 g of α-hexylcinnamylaldehyde dimethyl acetal (60 mmole) in 80 ml of dimethylformamide. After recrystallization from 80% ethanol, 5.2 g of product was obtained. NMR and IR spectra confirmed the title compound structure.

EXAMPLE VIII

4,6-O-(4'-Hydroxy-3'-methoxybenzylidene)-D-glucopyranose

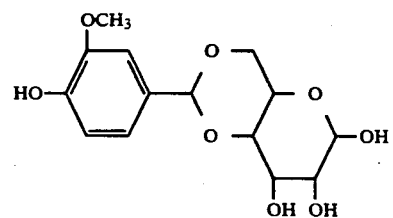

The title compound was prepared following the procedures of Example V, using 3.6 g (20 mmole) of glucose and 3×4.0 g (60 mmole) of vanillin dimethyl acetal. After removal of solvent and unreacted starting acetal by vacuum distillation, the residual material was recrystallized from 80/20 ethanol/10% ammonium hydroxide to give 5.1 g of product. NMR and IR spectra confirmed the title compound structure.

EXAMPLE IX

4,6-O-(3'-Ethoxy-4'-hydroxybenzylidene)-D-glucopyranose

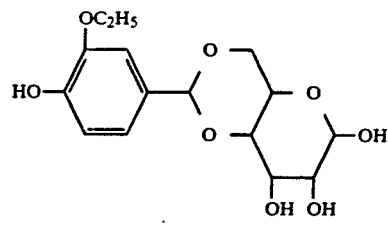

The title compound was prepared following the procedures of Example V, using 1.8 g of glucose and 3×2.12 g of ethyl vanillin dimethyl acetal. Isolation of the product (2.5 g ) was achieved by preparative HPLC. NMR and IR spectra confirmed the title compound structure.

EXAMPLE X

4,6-O-(3',4'-Dimethoxybenzylidene)-D-glucopyranose

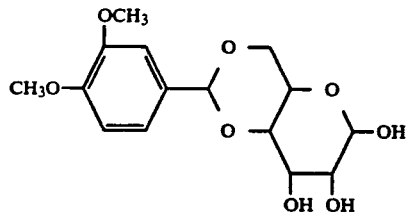

The title compound was prepared following the of Example V, using 3.6 g (20 mmole) of glucose and 3×4.24 g (60 mmole) of dimethoxybenzaldehyde dimethyl acetal. After recrystallization from 95% ethanol, 4.8 g of product was obtained. NMR and IR spectra confirmed the title compound structure.

EXAMPLE XI 4,6-O-(4'-Acetoxy-3'-methoxybenzylidene)-D-glucopyranose

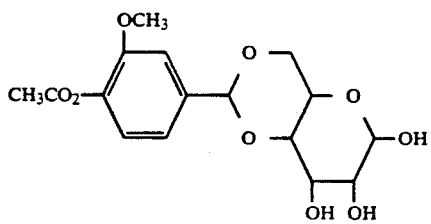

The title compound was prepared following the procedures of Example V, using 3.6 g (20 mmole) of glucose and 3×4.8 g (60 mmole) of vanillin acetate dimethyl acetal. Recrystallization from acetone yielded 5.1 g of product. NMR and IR spectra confirmed the title compound structure.

EXAMPLE XII 4,6-O-[α-(4'-Hydroxy-3'-methoxyphenyl)ethylidene]-D-glucopyranose

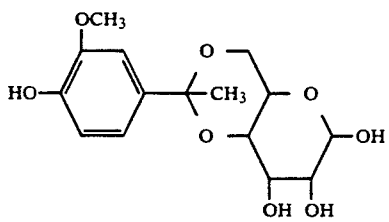

The title compound was prepared following the procedures of Example V, using 3.6 g (20 mmole) of glucose and 3×4.2 (60 mmole) of acetovanillone dimethyl ketal. After removal of solvent and unreacted starting ketal by vacuum distillation, the residual material was recrystallized from 80/20 ethanol/10% ammonium hydroxide to yield 4.1 g of product. NMR and IR spectra confirmed the title compound structure.

EXAMPLE XIII

This Example illustrates the relative flavorant-release efficiencies of 4,6-O-pyranose and 4,6-O-pyranoside derivatives under pyrolysis conditions in comparison with a methyl glucoside derivative.

The samples were analyzed by Curie Point Pyrolysis/GC/MS at 315° C. and 590° C. temperatures. The instruments utilized included Japan Analytical Industry JHP3S Pyroprobe, Varian 3400 Gas Chromatograph and a Finnigan 700 Ion Trap Mass Spec Detector (ITD). Samples of a flavorant-release compound (~30-45 μg) were pyrolyzed at each temperature for 5 seconds and the volatile products swept onto the head of a DB5-30M fused silica capillary column which was held at 0° C. After 4 minutes, the column oven was heated to 280° C. at 10°/minute. Detection was accomplished using the ITD, in the Electron Ionization mode. The relative amount of released flavorant material is calculated from the reconstructed chromatogram as area counts per microgram pyrolyzed.

| Compound | Area Count Per Microgram Pyrolyzed | |
|---|---|---|
| | 315° C. | 590° C. |
| Aromatek A-245[1] | $2.4 \times 10^5$ | $7.2 \times 10^5$ |
| Example III compound | $1.4 \times 10^5$ | $14.9 \times 10^5$ |
| Example V compound | $25.0 \times 10^5$ | $21.0 \times 10^5$ |

[1]Fritzsche, Dodge & Olcott. Methyl 4,6-O-(α-hexylcinnamylidene)-D-glucopyranoside.

The data demonstrated that invention pyranose and pyranoside derivatives exhibited a higher flavorant-release efficiency than a known methyl glucoside under pyrolysis conditions.

What is claimed is:

1. A smoking composition comprising an admixture of (1) combustible filler selected from natural tobacco, reconstituted tobacco and tobacco substitutes, and (2) between about 0.0001-5 weight percent, based on the total weight of filler, of a flavorant-release additive corresponding to the formula:

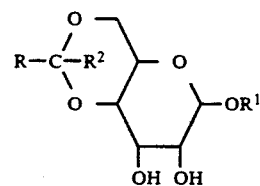

where R—C= is a $C_7$-$C_{12}$ benzylidene or $C_9$-$C_{15}$ cinnamylidene structure, $R^1$ is a monosaccharide or a $C_6$-$C_{10}$ aromatic substituent, and $R^2$ is hydrogen or a $C_1$-$C_6$ alkyl substituent.

2. A smoking composition in accordance with claim 1 wherein the flavorant-release additive is 4'-formyl-2'-methoxyphenyl 4,6-O-(α-hexylcinnamylidene)-β-D-glucopyranoside.

3. A smoking composition in accordance with claim 1 wherein the flavorant-release additive is 4'-formyl-2'-methoxyphenyl 4,6-O-(α-amylcinnamylidene)-β-D-glucopyranoside.

4. A smoking composition in accordance with claim 1 wherein the flavorant-release additive is 4'-formyl-2'-methoxyphenyl 4,6-O-cinnamylidene-β-D-glucopyranoside.

5. A smoking composition in accordance with claim 1 wherein the flavorant-release additive is 2'-methoxy-4'-methylphenyl 4,6-O-(α-hexylcinnamylidene)-α-D-glucopyranoside.

6. A cigarette smoking product comprising (1) a combustible filler selected from natural tobacco, reconstituted tobacco and tobacco substitutes, and (2) a paper wrapper which has incorporated therein a flavorant-release additive corresponding to the formula:

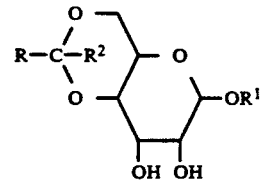

where R—C= is a $C_7$-$C_{12}$ benzylidene or $C_9$-$C_{15}$ cinnamylidene structure, $R^1$ is a monosaccharide or a $C_6$-$C_{10}$ aromatic substituent, and $R^2$ is hydrogen or a $C_1$-$C_6$ alkyl substituent.

7. A cigarette smoking product in accordance with claim 6 wherein the paper wrapper contains between about 0.01-5 weight percent of flavorant-release additive.

8. A cigarette smoking product in accordance with claim 6 wherein the flavorant-release additive is 4'-formyl-2'-methoxyphenyl 4,6-O-(α-hexylcinnamylidene)-β-D-glucopyranoside.

9. A cigarette smoking product in accordance with claim 6 wherein the flavorant-release additive is 4'-formyl-2'-methoxyphenyl 4,6-O-(α-amylcinnamylidene)-β-D-glucopyranoside.

10. A cigarette smoking produce in accordance with claim 6 wherein the flavorant-release additive is 4'-formyl-2'-methoxyphenyl 4,6-O-cinnamylidene-β-D-glucopyranoside.

11. A cigarette smoking product in accordance with claim 6 wherein the flavorant-release additive is 2'-methoxy-4'-methylphenyl 4,6-O-(α-hexylcinnamylidene)-α-D-glucopyranoside.

12. A cigarette smoking produce in accordance with claim 6 wherein the combustible filler contains between about 0.0001-5 weight percent, based on the weight of filler, of a flavorant-release additive corresponding to the formula:

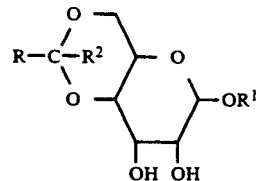

where R—C= is a $C_7$-$C_{12}$ benzylidene or $C_9$-$C_{15}$ cinnamylidene structure, $R^1$ is a monosaccharide or a $C_6$-$C_{10}$ aromatic substituent, and $R^2$ is hydrogen or a $C_1$-$C_6$ alkyl substituent.

13. A cigarette smoking product in accordance with claim 12 wherein the flavorant-release additive in the combustible filler is 4'-formyl-2'-methoxyphenyl 4,6-O-(α-hexylcinnamylidene)-β-D-glucopyranoside.

14. A cigarette smoking product in accordance with claim 12 wherein the flavorant-release additive is 4'-formyl-2'-methoxyphenyl 4,6-O-(α-amylcinnamylidene)-β-D-glucopyranoside.

15. A cigarette smoking product in accordance with claim 12 wherein the flavorant-release additive is 4'-formyl-2'-methoxyphenyl 4,6-O-cinnamylidene-β-D-glucopyranoside.

16. A cigarette smoking product in accordance with claim 12 wherein the flavorant-release additive is 2'-methoxy-4'-methylphenyl 4,6-O-(α-hexylcinnamylidene)-α-D-glucopyranoside.

17. 4'-Formyl-2-'-methoxyphenyl 4,6-O-(α-hexylcinnamylidene)-β-D-glucopyranoside.

18. 4'-Formyl-2'-methoxyphenyl 4,6-O-(α-amylcinnamylidene)-β-D-glucopyranoside.

19. 4'-Formyl-2'-methoxyphenyl 4,6-O-cinnamylidene-β-D-glucopyranoside.

20. 2'-Methoxy-4'-methylphenyl 4,6-O-(α-hexylcinnamylidene)-α-D-glucopyranoside.

* * * * *

UNITED STATES PATENT AND TRADEMARK OFFICE
CERTIFICATE OF CORRECTION

PATENT NO. : 5,137,578
DATED : August 11, 1992
INVENTOR(S) : W.G. Chan

It is certified that error appears in the above-indentified patent and that said Letters Patent is hereby corrected as shown below:

On the title page, Item [75] Inventor: should read --Woontung G. Chan--

Col. 2, line 12, "qlucopyranoside" should be --glucopyranoside--.

Col. 11, Claim 10, line 20, "produce" should be --product--.
Col. 11, Claim 12, line 33, "produce" should be --product--.

Signed and Sealed this

Second Day of November, 1993

Attest:

BRUCE LEHMAN

Attesting Officer

Commissioner of Patents and Trademarks